US012661011B2

(12) United States Patent　　(10) Patent No.:　US 12,661,011 B2
Shibata et al.　　　　　　　　　　(45) Date of Patent:　　Jun. 23, 2026

(54) BIOLOGICAL INFORMATION ACQUISITION DEVICE

(71) Applicant: Sharp Semiconductor Innovation Corporation, Tenri City (JP)

(72) Inventors: Keiichi Shibata, Tenri City (JP); Daisuke Funao, Tenri City (JP); Kunihiko Kitaoku, Tenri City (JP); Sota Hida, Tenri City (JP); Yuta Mochizuki, Tenri City (JP)

(73) Assignee: Sharp Semiconductor Innovation Corporation, Tenri City (JP)

( * ) Notice: Subject to any disclaimer, the term of this patent is extended or adjusted under 35 U.S.C. 154(b) by 267 days.

(21) Appl. No.: 18/545,162

(22) Filed: Dec. 19, 2023

(65) Prior Publication Data

US 2024/0206735 A1　　Jun. 27, 2024

(30) Foreign Application Priority Data

Dec. 26, 2022　　(JP) ................................. 2022-208414

(51) Int. Cl.
　　*G06K 9/00*　　　　(2022.01)
　　*A61B 5/00*　　　　(2006.01)
　　　　　　(Continued)

(52) U.S. Cl.
　　CPC ............ *A61B 5/0082* (2013.01); *A61B 5/021* (2013.01); *A61B 5/0261* (2013.01); *G06T 7/0012* (2013.01); *G06T 2207/10048* (2013.01); *G06T 2207/20084* (2013.01); *G06T 2207/30104* (2013.01)

(58) Field of Classification Search
　　CPC ... A61B 5/0082; A61B 5/021; A61B 5/02416; A61B 5/0261; G06T 2207/10048; G06T 2207/20084; G06T 2207/30104; G06T 7/0012
　　See application file for complete search history.

(56) References Cited

U.S. PATENT DOCUMENTS

2012/0197137 A1 *　8/2012　Jeanne ................. A61B 5/0261
　　　　　　　　　　　　　　　　　　　　　　600/479
2014/0192177 A1 *　7/2014　Bartula ................. G06T 7/0016
　　　　　　　　　　　　　　　　　　　　　　348/77

(Continued)

FOREIGN PATENT DOCUMENTS

WO　　　2017/104056 A1　　6/2017

*Primary Examiner* — Hadi Akhavannik
(74) *Attorney, Agent, or Firm* — ScienBiziP, P.C.

(57) ABSTRACT

A biological information acquisition device includes a near-infrared light source, a solid-state image sensor, and an information processing device, wherein the solid-state image sensor includes at least one specific pixel having a sensitivity peak in a specific wavelength band of 620 nm or more and 1100 nm or less, the information processing device is configured to repeatedly acquire (i) an emission image frame captured by the solid-state image sensor during an emission period of the near-infrared light source and (ii) a non-emission image frame captured by the solid-state image sensor during a non-emission period of the near-infrared light source, and the information processing device is configured to derive biological information on the basis of the emission image frame and the non-emission image frame.

9 Claims, 9 Drawing Sheets

(51) Int. Cl.
  *A61B 5/021*   (2006.01)
  *A61B 5/026*   (2006.01)
  *G06T 7/00*   (2017.01)

(56)     References Cited

U.S. PATENT DOCUMENTS

2015/0297142 A1* 10/2015 De Jaam .............. A61B 5/7278
                  600/407
2017/0178326 A1   6/2017 Fukunishi
2018/0073873 A1*  3/2018 Takao ................ G03B 21/2053
2021/0030291 A1*  2/2021 Watanabe .............. A61B 6/563
2024/0206735 A1*  6/2024 Shibata ................. A61B 5/021

* cited by examiner

BIOLOGICAL INFORMATION ACQUISITION DEVICE

CROSS-REFERENCE TO RELATED APPLICATION

The present application claims priority from Japanese Application JP 2022-208414, the content of which is hereby incorporated by reference into this application.

BACKGROUND OF THE INVENTION

Field of the Invention

An aspect of the disclosure relates to a biological information acquisition device.

Description of the Related Art

WO 2017/104056 discloses an example of a configuration of a device for acquiring biological information (e.g., a pulse volume).

SUMMARY

There is a demand to acquire more accurate biological information.

A biological information acquisition device according to an aspect of the disclosure to meet the desire is a biological information acquisition device that acquires biological information of a living body in a non-contact manner, the biological information acquisition device including a near-infrared light source configured to emit near-infrared light having an intensity peak in a near-infrared wavelength band of 760 nm or more and 1100 nm or less toward the living body, a solid-state image sensor configured to capture an image of the living body by receiving light arriving from the living body, and an information processing device configured to derive the biological information on the basis of the image, wherein the solid-state image sensor includes at least one specific pixel having a sensitivity peak in a specific wavelength band of 620 nm or more and 1100 nm or less, the information processing device is configured to repeatedly acquire (i) an emission image frame captured by the solid-state image sensor during an emission period of the near-infrared light source and (ii) a non-emission image frame captured by the solid-state image sensor during a non-emission period of the near-infrared light source, and the information processing device is configured to derive the biological information on the basis of the emission image frame and the non-emission image frame.

According to an aspect of the disclosure, it is possible to acquire biological information with higher accuracy than before.

DETAILED DESCRIPTION OF THE INVENTION

First Embodiment

Figure 1:
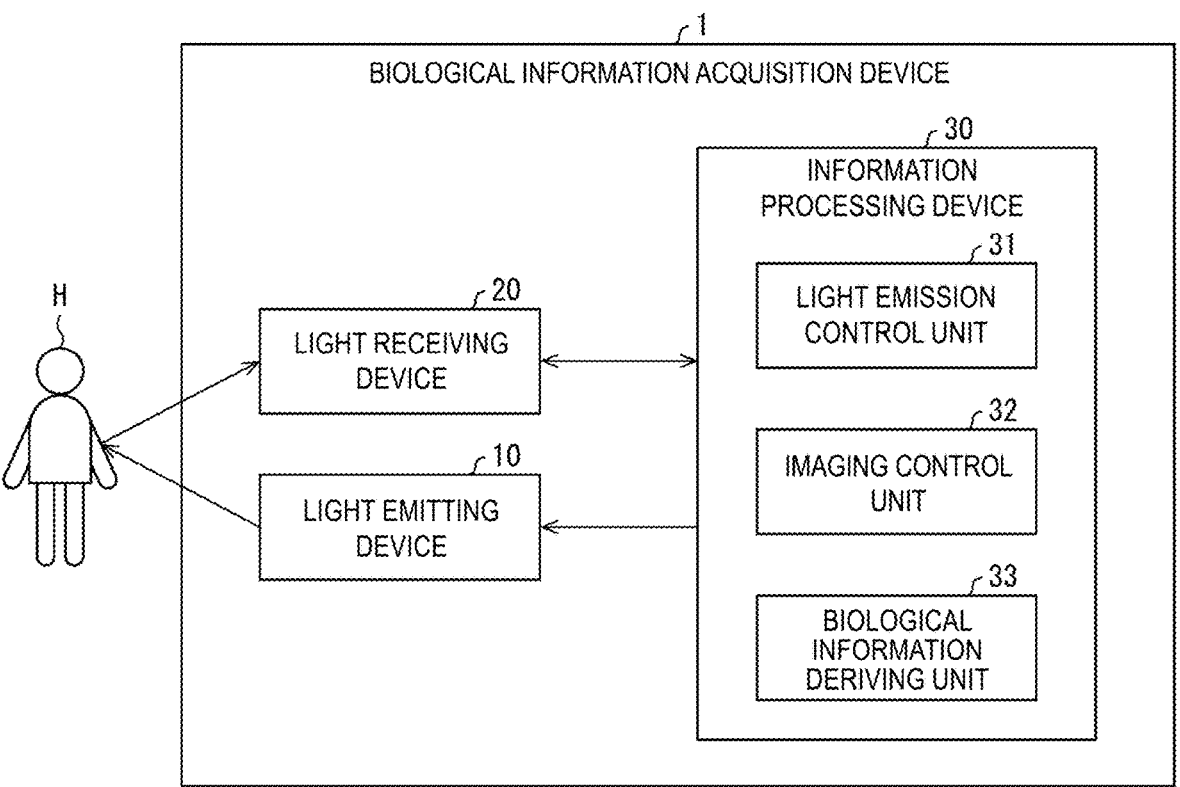
FIG. 1 is a block diagram illustrating a configuration of main parts of a biological information acquisition device according to a first embodiment.

A first embodiment will be described below. In each of the subsequent embodiments, components having the same functions as components described in the first embodiment are given the same reference numerals for convenience of explanation and description thereof will not be repeated. Description of known technical matters will be omitted as appropriate for the sake of brevity. Components and numerical values described in this specification are all merely examples unless otherwise contradicted. Thus, for example, the positional relationship and the number of components are not limited to the examples shown in the drawings unless otherwise stated. Further, the drawings are not necessarily drawn to scale.

Example of Configuration of Biological Information Acquisition Device 1

FIG. 1 is a block diagram illustrating a configuration of main parts of a biological information acquisition device 1 according to the first embodiment. The biological information acquisition device 1 acquires biological information of a living body H in a non-contact manner. The living body H is not particularly limited as long as it is a living object whose biological information can be acquired by the biological information acquisition device 1. In FIG. 1, a human being is illustrated as the living body H. The biological information acquisition device 1 includes a light emitting device 10, a light receiving device 20, and an information processing device 30. In this specification, near-infrared light is also referred to as infrared (IR) light. Thus, for example, a near-infrared light source is also referred to as an IR light source.

Figure 2:
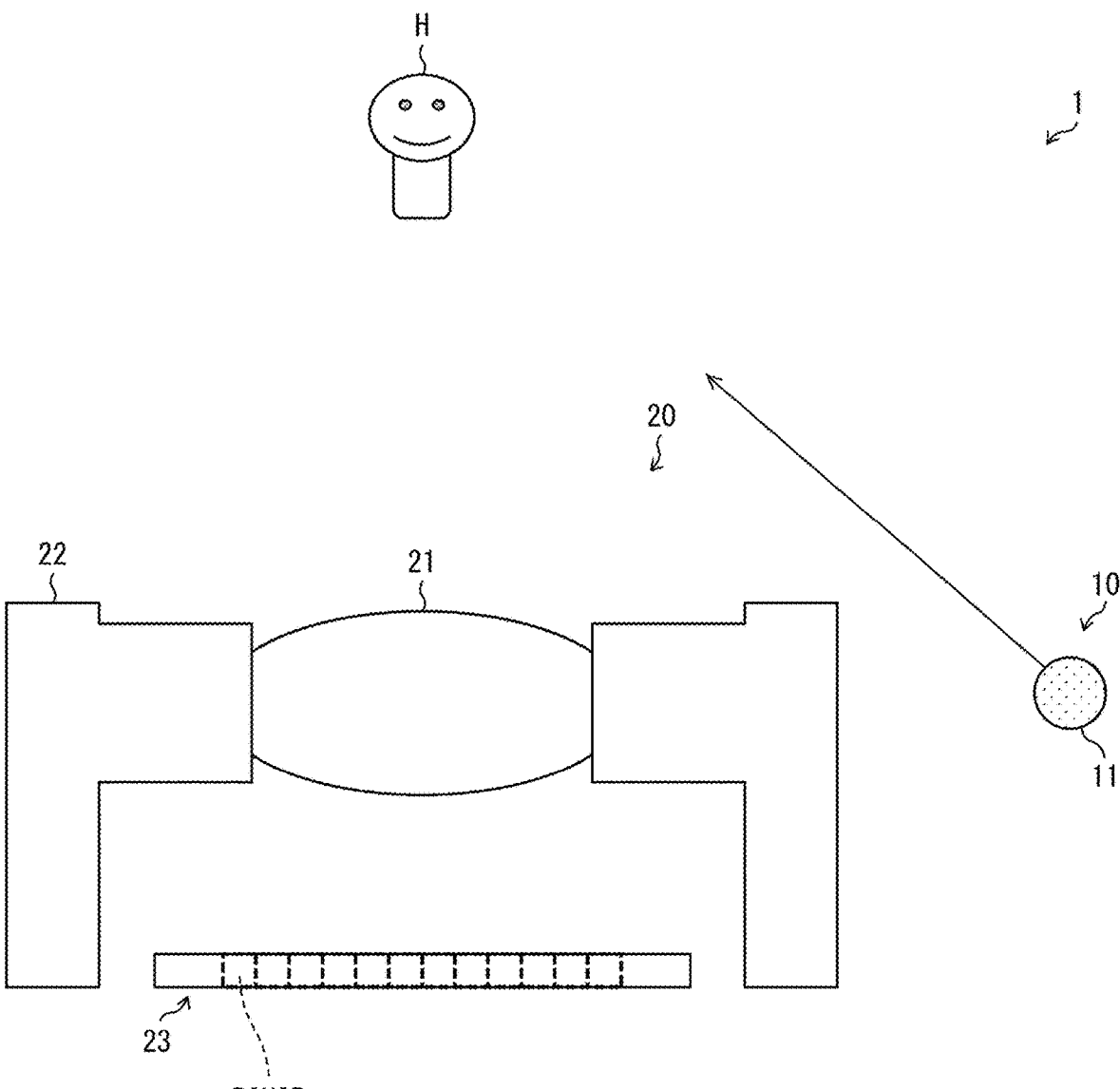
FIG. 2 is a schematic front view illustrating an example of a configuration of a light receiving device according to the first embodiment.

The light emitting device 10 emits test light for acquiring biological information of the living body H. The light emitting device 10 includes an IR light source 11, as illustrated in FIG. 2 to be described later. The IR light source 11 emits near-infrared light as test light. Specifically, the IR light source 11 emits IR light toward the living body H, the IR light having an intensity peak in a near-infrared wavelength band (an IR wavelength band) of 760 nm or more and 1100 nm or less.

By using IR light which is invisible light as the test light, it is possible to make the living body H unaware of the presence of the test light. Thus, it is possible to acquire biological information of the living body H in a natural state. However, the test light is not limited to IR light as is apparent to those skilled in the art. Thus, the light emitting device 10 may further include an additional light source that emits light (e.g., visible light) having a peak outside the IR wavelength band as test light.

The light receiving device 20 includes a solid-state image sensor that captures an image of the living body H (hereinafter simply referred to as an "image") by receiving light arriving from the living body H. The image in the first embodiment may be any image that shows a predetermined part of the living body H (e.g., a face image of the living body H). The solid-state image sensor 23 in FIG. 2 is an example of a solid-state image sensor according to an aspect of the disclosure. The solid-state image sensor may be a CMOS image sensor (CIS) or a charge coupled device (CCD). The solid-state image sensor has a plurality of pixels as will be described later.

The information processing device 30 derives biological information of the living body H on the basis of the image captured by the solid-state image sensor 23. The information processing device 30 may derive biological information by analyzing the image (more specifically, by performing signal processing on the image). Thus, biological information can be acquired in a non-contact manner. The case where the information processing device 30 derives a pulse volume of a living body H as biological information will be mainly illustrated in the first embodiment.

The information processing device 30 in the example of FIG. 1 may be a control device that centrally controls each part of the biological information acquisition device 1. Thus, the information processing device 30 may control the light emitting device 10 and the light receiving device 20. The information processing device 30 may control the light receiving device 20 such that the solid-state image sensor 23 captures images at a predetermined frame rate. In this specification, images captured at a predetermined frame rate are also referred to as image frames. The information processing device 30 may also control the emission of IR light by the IR light source 11.

In the example of the first embodiment, it is assumed that the space where the living body H is present is illuminated by environmental light. It is also assumed that the environmental light is white light. Part of the environmental light is reflected by the living body H (more specifically, the skin of the living body H) and incident on the light receiving device 20. Thus, the solid-state image sensor 23 receives white light reflected by the living body H during a non-emission period of the IR light source 11 (a period during which the IR light source 11 does not emit near-infrared light). In this way, the solid-state image sensor 23 captures an image according to the received white light during the non-emission period.

On the other hand, the solid-state image sensor 23 additionally receives near-infrared light reflected by the living body H during an emission period of the IR light source 11 (a period during which the IR light source 11 emits near-infrared light). Thus, the solid-state image sensor 23 captures an image according to the received white light and near-infrared light during the emission period.

In the example of the first embodiment, it is assumed that the intensity of IR light emitted from the IR light source 11 is set to be greater than the intensity of the environmental light. Accordingly, the image captured by the solid-state image sensor 23 during the emission period of the IR light source 11 mainly depends on the IR light emitted from the IR light source 11. Therefore, the image captured by the solid-state image sensor 23 during the emission period may be referred to as an IR image. On the other hand, the image captured by the solid-state image sensor 23 during the non-emission period may be referred to as a visible light image.

As shown in FIG. 1, the information processing device 30 may include a light emission control unit 31, an imaging control unit 32, and a biological information deriving unit 33. An example of processing performed by the information processing device 30 will be described later.

FIG. 2 is a schematic front view illustrating an example of a configuration of the light receiving device 20. The light receiving device 20 may include a light guide member 21, a support member 22, and a solid-state image sensor 23. In FIG. 2, the IR light source 11 and the living body H are also illustrated for convenience of explanation. As shown in FIG. 2, the IR light source 11 and the light receiving device 20 are spaced apart from the living body H. The positional relationship between the IR light source 11 and the light receiving device 20 only needs to be set such that the IR light emitted by the IR light source 11 and reflected by the living body H is incident on the light receiving device 20. In an example, the IR light source 11 may be placed near the light receiving device 20.

The light guide member 21 guides the light incident on the light receiving device 20 to the solid-state image sensor 23. In FIG. 2, a lens is illustrated as the light guide member 21. The support member 22 supports the light guide member 21. The support member 22 in the example of FIG. 2 is a lens holder.

In this specification, a wavelength band of 620 nm or more and 1100 nm or less is referred to as a specific wavelength band. A wavelength band of 620 nm or more and 740 nm or less is referred to as a first wavelength band and a wavelength band of 350 nm or more and 590 nm or less is referred to as a second wavelength band.

In this specification, a pixel having a sensitivity peak in the specific wavelength band is referred to as a specific pixel. A pixel having a sensitivity peak in the IR wavelength band is referred to as an IR pixel (a near-infrared pixel). A pixel having a sensitivity peak in the first wavelength band is referred to as a first pixel and a pixel having a sensitivity peak in the second wavelength band is referred to as a second pixel.

As is apparent to those skilled in the art, a red (R) wavelength band belongs to the first wavelength band. Thus, an R pixel described in a second embodiment below is an example of a first pixel. As is apparent from the above example, the specific wavelength band includes the entire IR wavelength band and the entire first wavelength band. Thus, both an IR pixel and an R pixel described herein are examples of a specific pixel.

As is apparent to those skilled in the art, both a blue (B) wavelength band and a green (G) wavelength band belong to the second wavelength band. Thus, both a B pixel and a G pixel described in the second embodiment are examples of a second pixel.

A solid-state image sensor according to an aspect of the disclosure only needs to have specific pixels. Thus, the solid-state image sensor 23 may include, for example, IR pixels PIXIR as shown in FIG. 2.

Figure 3:
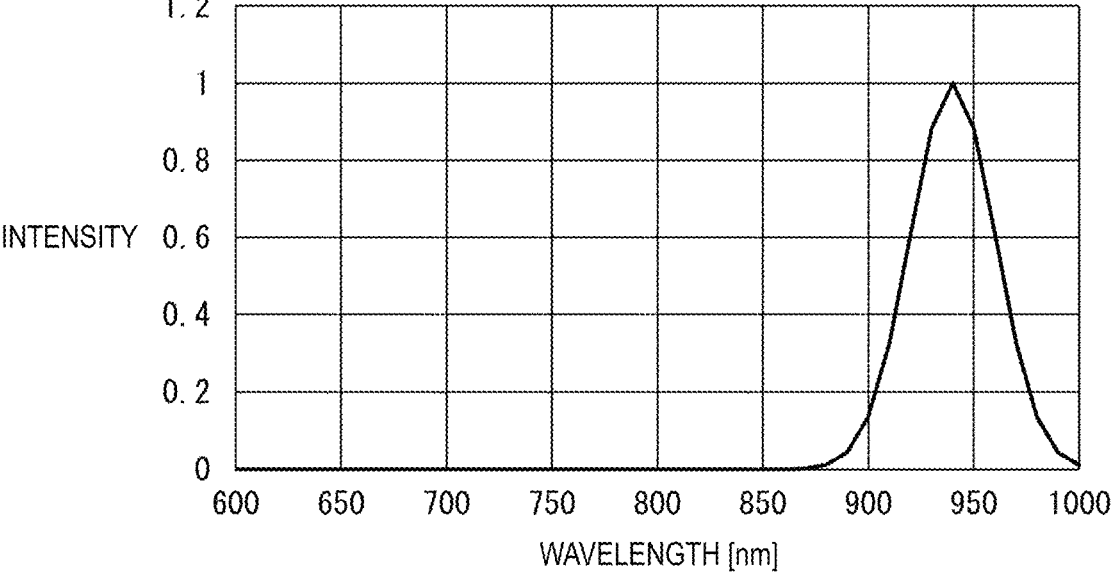
FIG. 3 illustrates a wavelength spectrum of IR light emitted from an IR light source.

FIG. 3 is a graph illustrating a wavelength spectrum of IR light emitted from the IR light source 11. In FIG. 3, the horizontal axis represents the wavelength of light and the vertical axis represents the intensity of light. The vertical axis in FIG. 3 is normalized. The IR light in the example of FIG. 3 has an intensity peak at or near a wavelength of 940 nm. Thus, the solid-state image sensor 23 may be designed to have a sensitivity peak in the IR wavelength band. In this case, IR pixels can be realized without providing a spectral filter.

However, IR pixels may also be realized by providing a spectral filter as will be described in the second embodiment. The solid-state image sensor 23 may also include pixels other than IR pixels as is apparent from the second embodiment. Pixels other than IR pixels may be monochrome pixels or color pixels.

Figure 4:
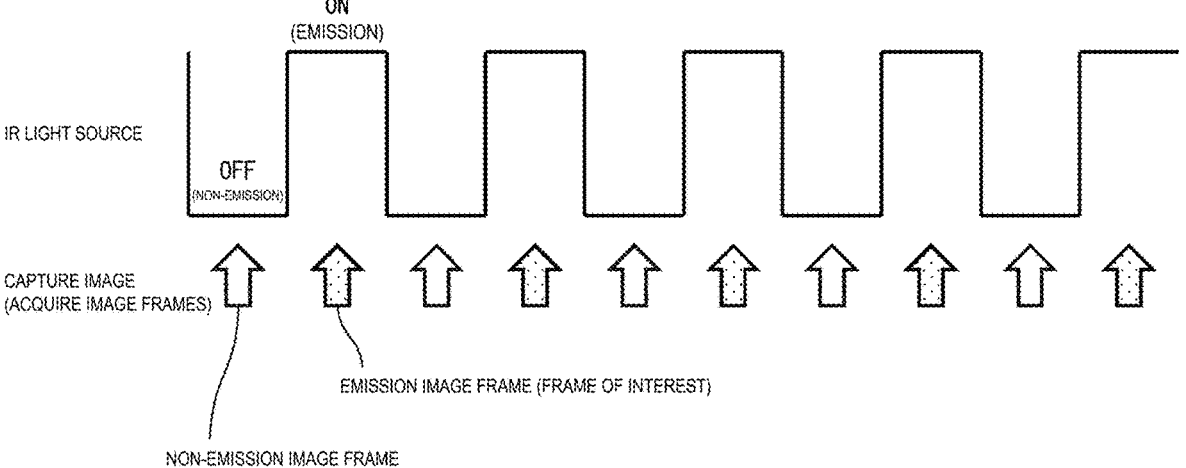
FIG. 4 is a diagram illustrating an example of processing performed by an information processing device.

Next, an example of processing performed by the information processing device 30 will be described with reference to FIG. 4. The light emission control unit 31 may set light emission times of the IR light source 11. Thus, the light emission control unit 31 may set, for example, emission periods (ON periods) and non-emission periods (OFF periods) of the IR light source 11. As shown in FIG. 4, the light emission control unit 31 may control the IR light source 11 such that emission periods and non-emission periods arrive alternately. In the example of FIG. 4, the length of each emission period and the length of each non-emission period are set to be equal.

The imaging control unit 32 may control the solid-state image sensor 23 such that it captures one image in each of the non-emission periods and the emission periods. In this way, the information processing device 30 may control the IR light source 11 and the solid-state image sensor 23 such that the emission/non-emission operation of the IR light source 11 and the imaging operation of the solid-state image sensor 23 are synchronized. Synchronization between the IR light source 11 and the solid-state image sensor 23 is achieved by setting the frame rate of the solid-state image sensor 23 according to the emission period and the non-emission period. In the example of FIG. 4, the frame rate of the solid-state image sensor 23 is set to a value equal to the reciprocal of the length of each emission period.

In this specification, an image captured by the solid-state image sensor 23 during an emission period is referred to as an emission image frame. On the other hand, an image captured by the solid-state image sensor 23 during a non-emission period is referred to as a non-emission image frame. The information processing device 30 may repeatedly acquire emission image frames and non-emission image frames. Thus, the imaging control unit 32 may control the solid-state image sensor 23 to alternately capture emission image frames and non-emission image frames as shown in FIG. 4.

The biological information deriving unit 33 may derive biological information on the basis of the repeatedly acquired emission image frames and non-emission image frames. Hereinafter, an example of a method for deriving biological information on the basis of emission image frames and non-emission image frames will be described.

In this specification, an arbitrary one of a plurality of emission image frames is referred to as a frame of interest. The time at which the frame of interest is captured is referred to as a time of interest. A non-emission image frame captured prior to the time of interest is referred to as a first reference frame. On the other hand, a non-emission image frame captured subsequent to the time of interest is referred to as a second reference frame.

In a first example, the biological information deriving unit 33 may average signal values (e.g., pixel values) of a predetermined region (a skin region) in which the skin of the living body H is reflected in the frame of interest. Then, the biological information deriving unit 33 may average signal values of the skin region in one non-emission image frame corresponding to the frame of interest. The non-emission image frame corresponding to the frame of interest may be a first reference frame (e.g., a non-emission image frame immediately before the frame of interest). Alternatively, the non-emission image frame may be a second reference frame (e.g., a non-emission image frame immediately after the frame of interest).

Next, the biological information deriving unit 33 may subtract the average signal value (the average of signal values) of the skin region in the corresponding non-emission image frame from the average signal value of the skin region in the frame of interest. In this way, the biological information deriving unit 33 may correct the signal value of the frame of interest using the signal value of the corresponding non-emission image frame. Then, the biological information deriving unit 33 may derive a pulse volume on the basis of the corrected frame of interest.

For example, the biological information deriving unit 33 may correct signal values of a plurality of emission image frames as described above. Then, the biological information deriving unit 33 may derive a pulse volume on the basis of the signal values of the plurality of emission image frames that have been corrected. A non-emission image frame may be used as a reference frame for correcting an emission image frame as described above. Namely, a signal value of a non-emission image frame may be used as a reference frame for correcting a signal value of an emission image frame.

Generally, signal components of a pulse volume (hereinafter referred to as pulse volume components) are relatively small. Noise components may also be superimposed on pulse volume components in an image captured by a solid-state image sensor. Noise components are caused, for example, by fluctuations in the amount of environmental light and body movements of the living body H. The biological information deriving unit 33 can reduce noise components included in emission image frames by correcting the emission image frames using non-emission image frames. Next, a pulse volume can be derived using the corrected emission image frames (the emission image frames in which noise components have been reduced), such that a more accurate pulse volume can be obtained.

Figure 5:
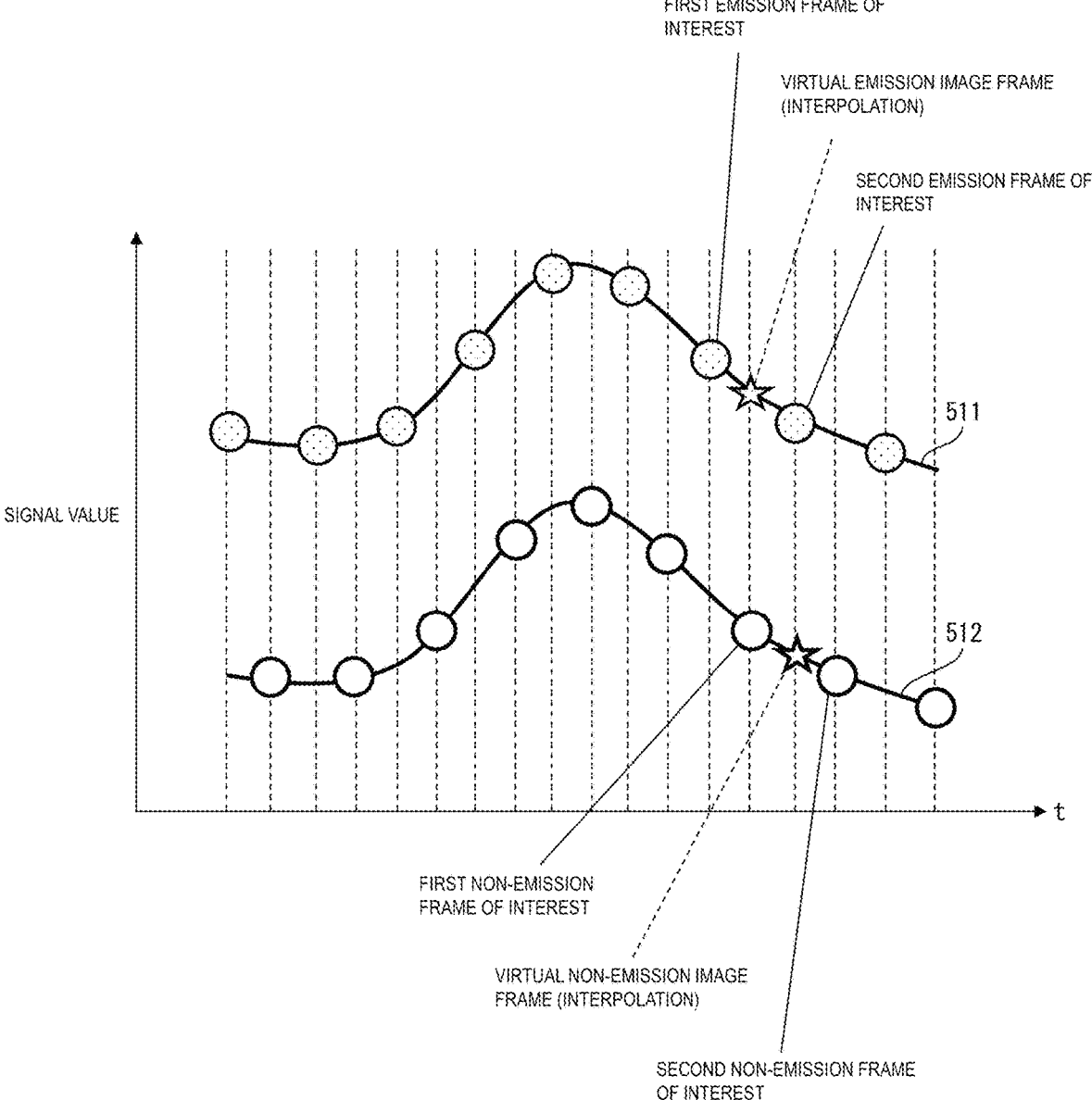
FIG. 5 is a schematic graph showing temporal changes in signal values of emission image frames and non-emission image frames.

Next, a second example will be described with reference to FIG. 5. FIG. 5 is a schematic graph showing temporal changes in signal values of emission image frames and non-emission image frames. The horizontal axis in the graph is time (t) and the vertical axis is signal value. A curve 511 in FIG. 5 is an interpolation curve (a fitting curve) obtained by interpolating between the signal values of emission image frames at times. On the other hand, a curve 512 is an interpolation curve obtained by interpolating between the signal values of non-emission image frames at times.

In the description of the second example, an arbitrary one of a plurality of emission image frames is referred to as a first emission frame of interest. An emission image frame following the first emission frame of interest is referred to as a second emission frame of interest. The time at which the first emission frame of interest is captured is referred to as a first emission time of interest and the time at which the second emission frame of interest is captured is referred to as a second emission time of interest.

The biological information deriving unit 33 may generate a virtual emission image frame in a non-emission period between the first emission time of interest and the second emission time of interest on the basis of the first emission frame of interest and the second emission frame of interest. Specifically, the biological information deriving unit 33 may obtain a signal value of the virtual emission image frame through interpolation on the basis of the signal value of the first emission frame of interest and the signal value of the second emission frame of interest as shown in FIG. 5. In an example, the biological information deriving unit 33 may obtain the signal value of a virtual emission image frame through interpolation using the signal value of the first emission frame of interest and the signal value of the second emission frame of interest.

However, the method of interpolation to obtain the signal value of the virtual emission image frame is not limited to the above example. Signal values of one or more emission image frames earlier than the first emission frame of interest may further be used for interpolation to obtain the signal value of the virtual emission image frame. That is, the signal values of a plurality of emission image frames earlier than a virtual emission image frame may be used for interpolation to obtain the signal value of the virtual emission image frame.

The signal values of one or more emission image frames later than the second emission frame of interest may further be used for interpolation to obtain the signal value of the virtual emission image frame. That is, the signal values of a plurality of emission image frames later than a virtual emission image frame may be used for interpolation to obtain the signal value of the virtual emission image frame.

Thus, both (i) the signal values of a plurality of emission image frames earlier than a virtual emission image frame and (ii) the signal values of a plurality of emission image frames later than the virtual emission image frame may be used for interpolation to obtain the signal value of the virtual emission image frame.

Next, interpolation of non-emission image frames will be described. In the description of the second example, an arbitrary one of a plurality of non-emission image frames is referred to as a first non-emission frame of interest. A non-emission image frame following the first non-emission frame of interest is referred to as a second non-emission frame of interest. The time at which the first non-emission frame of interest is captured is referred to as a first non-emission time of interest and the time at which the second non-emission frame of interest is captured is referred to as a second non-emission time of interest.

The biological information deriving unit 33 may generate a virtual non-emission image frame in an emission period between the first non-emission time of interest and the second non-emission time of interest on the basis of the first non-emission frame of interest and the second non-emission frame of interest. Specifically, the biological information deriving unit 33 may obtain a signal value of the virtual non-emission image frame through interpolation on the basis of the signal value of the first non-emission frame of interest and the signal value of the second non-emission frame of interest as shown in FIG. 5. In an example, the biological information deriving unit 33 may obtain the signal value of a virtual non-emission image frame through interpolation using the signal value of the first non-emission frame of interest and the signal value of the second non-emission frame of interest.

However, the method of interpolation to obtain the signal value of the virtual non-emission image frame is not limited to the above example. Signal values of one or more non-emission image frames earlier than the first non-emission frame of interest may further be used for interpolation to obtain the signal value of the virtual non-emission image frame. That is, the signal values of a plurality of non-emission image frames earlier than a virtual non-emission image frame may be used for interpolation to obtain the signal value of the virtual non-emission image frame.

The signal values of one or more non-emission image frames later than the second non-emission frame of interest may further be used for interpolation to obtain the signal value of the virtual non-emission image frame. That is, the signal values of a plurality of non-emission image frames later than a virtual non-emission image frame may be used for interpolation to obtain the signal value of the virtual non-emission image frame.

Thus, both (i) the signal values of a plurality of non-emission image frames earlier than a virtual non-emission image frame and (ii) the signal values of a plurality of non-emission image frames later than the virtual non-emission image frame may be used for interpolation to obtain the signal value of the virtual non-emission image frame.

In the second example, the biological information deriving unit 33 may derive a pulse volume further on the basis of signal values of virtual emission image frames. The biological information deriving unit 33 can also derive a pulse volume on the basis of signal values of virtual non-emission image frames. According to the second example, a pulse volume can be derived using data of more signal values than in the first example. Thus, according to the second example, it is possible to obtain a more accurate pulse volume than in the first example.

Effects of Biological Information Acquisition Device 1

The technique itself for detecting biological information (e.g., a pulse volume) using a solid-state image sensor is well known. However, general solid-state image sensors are designed for the purpose of capturing images of subjects in the visible light range. Human eyes have high visual sensitivity in the G wavelength band. Hemoglobin contained in the skin of a living body has a particularly high light absorption rate at a wavelength of 550 nm belonging to the G wavelength band. Thus, in the related art, general solid-state image sensors have been used without modification in the derivation of a pulse volume.

For example, the technique disclosed in WO 2017/104056 acquires a received optical signal of blue light, a received optical signal of green light, and a received optical signal of red light using a general solid-state image sensor. The technique disclosed in WO 2017/104056 uses the received optical signal of red light or the received optical signal of blue light as a reference signal for the received optical signal of green light. Specifically, the technique disclosed in WO 2017/104056 uses the reference signal to perform signal processing for removing noise components from the received optical signal of green light which is a signal of interest.

A general solid-state image sensor is designed to receive red light having an intensity peak in a wavelength band around 600 nm and blue light having an intensity peak in a wavelength band around 450 nm. However, in these wavelength bands, the received optical signal of red light or the received optical signal of blue light includes pulse volume components that are large to some extent. Therefore, signal processing of the technique of WO 2017/104056 reduces pulse volume components included in the signal of interest as it removes noise components using a reference signal. Moreover, the idea of using IR light as test light is not mentioned at all in the technique of WO 2017/104056.

The inventors of the present application (hereinafter abbreviated as "inventors") have newly devised a biological information acquisition device according to an aspect of the disclosure (e.g., the biological information acquisition device 1) in view of the above problems of the technique of WO 2017/104056. The inventors have discovered through experiments that the light absorption rate of hemoglobin is particularly small in the first wavelength band described above. On the basis of this new knowledge, the inventors have further discovered a new idea of using a non-emission image frame as a reference frame.

The light absorption rate of hemoglobin in the IR wavelength band is higher than the light absorption rate in the first wavelength band. Thus, a solid-state image sensor having specific pixels (e.g., the solid-state image sensor 23 having IR pixels) can obtain an emission image frame including larger pulse volume components than a non-emission image frame. Therefore, use of the non-emission image frame as a reference frame can reduce noise components in the emission image frame without reducing pulse volume components too much. Accordingly, signal processing of a biological information acquisition device according to an aspect of the disclosure can acquire a pulse volume with higher accuracy than the technique disclosed in WO 2017/104056. When biological information is acquired in a non-contact manner, noise components generally tend to be larger than when biological information is acquired in a contact manner. A biological information acquisition device according to an aspect of the disclosure can acquire an accurate pulse volume even when biological information is acquired in a non-contact manner.

As is apparent to those skilled in the art, a biological information acquisition device according to an aspect of the disclosure can further derive other biological information on the basis of a pulse volume. For example, the biological information acquisition device can acquire the heart rate, blood pressure, stress level, or the like of the living body on the basis of the pulse volume. As described above, a biological information acquisition device according to an aspect of the disclosure can acquire biological information other than a pulse volume with higher accuracy than before.

Second Embodiment

Figure 6:
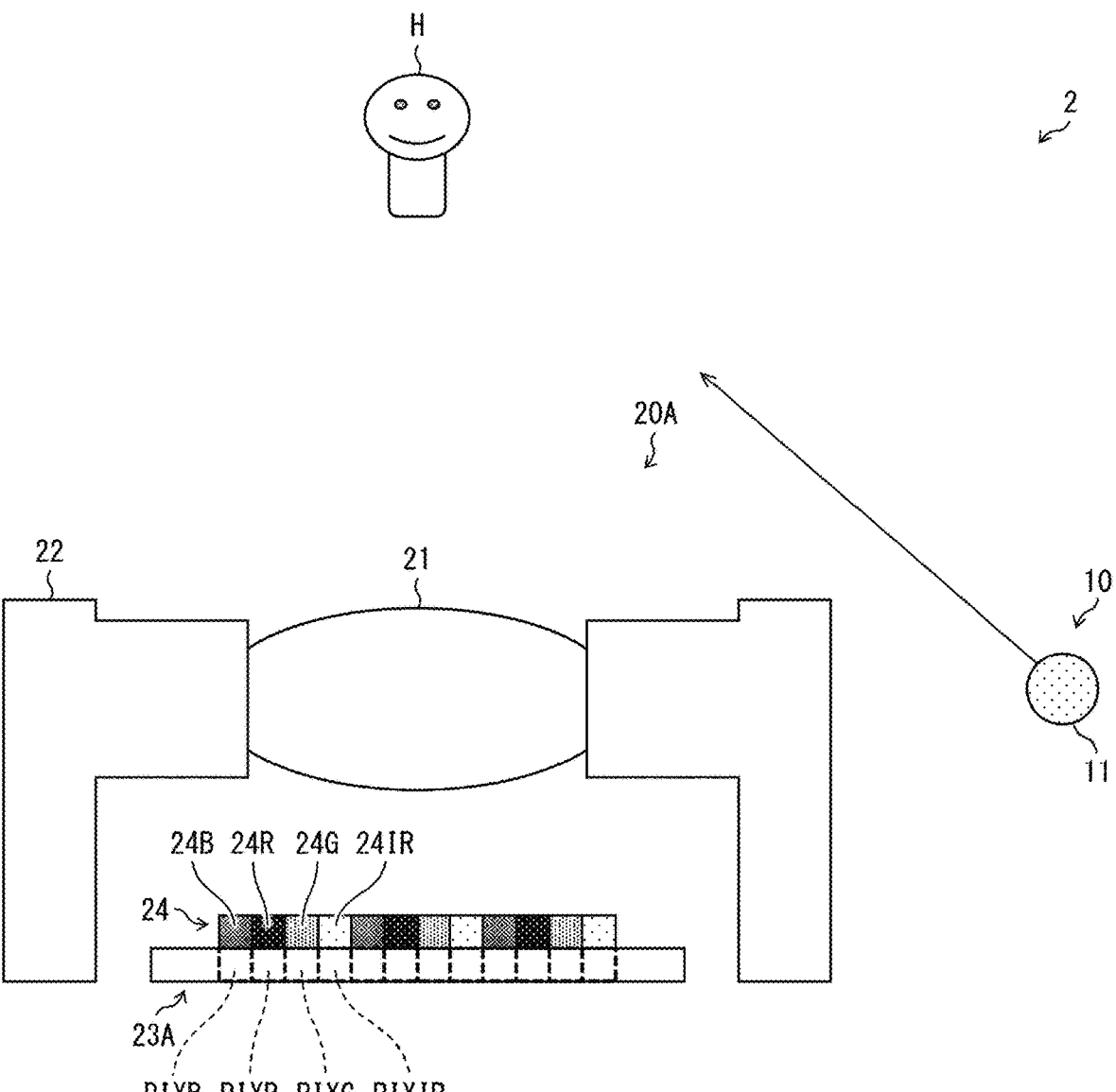
FIG. 6 is a schematic front view illustrating an example of a configuration of a light receiving device according to a second embodiment.

FIG. 6 is a schematic front view illustrating an example of a configuration of a light receiving device 20A in a biological information acquisition device 2 according to the second embodiment. FIG. 6 is a diagram corresponding to FIG. 2. A solid-state image sensor in the light receiving device 20A is referred to as a solid-state image sensor 23A.

The light receiving device 20A may include a spectral filter 24. The spectral filter 24 in the example of FIG. 6 includes red light filters 24R, blue light filters 24B, green light filters 24G, and near-infrared light filters 24IR. In this specification, a spectral filter that transmits light in the first wavelength band is referred to as a first filter and a spectral filter that transmits light in the second wavelength band is referred to as a second filter. The red light filters 24R are examples of a first filter. Both the blue light filters 24B and the green light filters 24G are examples of a second filter.

The first filter (e.g., each red light filter 24R) ideally has spectral characteristics that selectively transmits only light in the first wavelength band (e.g., red light). Thus, the first filter has high light transmittance (ideally, light transmittance of 100%) in the first wavelength band (e.g., the R wavelength band) and has low light transmittance (ideally, light transmittance of 0%) in wavelength bands excluding the first wavelength band. This description regarding the light transmittance of the first filter applies similarly to spectral filters corresponding to other wavelength bands.

Figure 7:
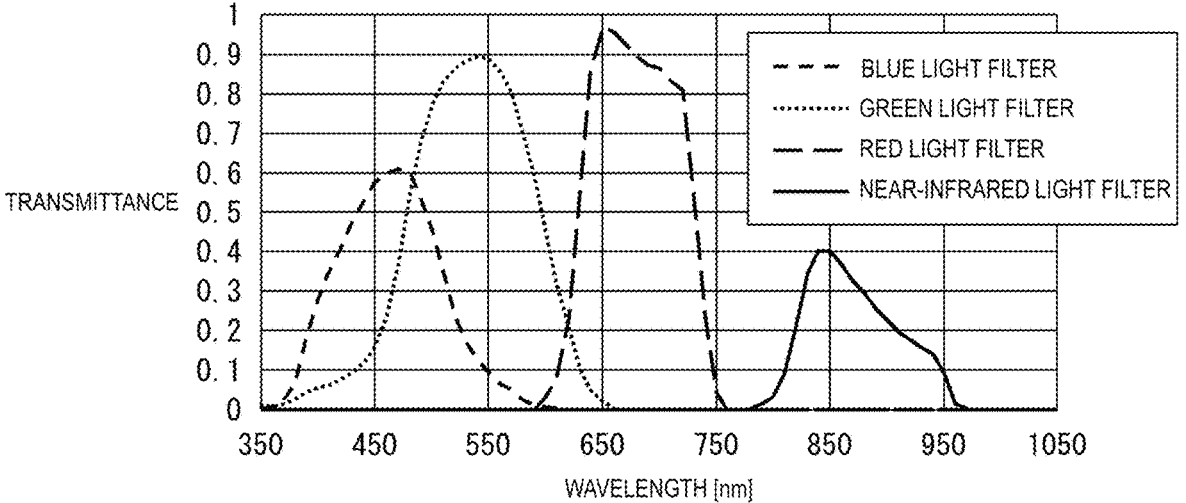
FIG. 7 illustrates spectral characteristics of the light receiving device according to the second embodiment.

FIG. 7 is a graph illustrating spectral characteristics of the light receiving device 20A of FIG. 6 (specifically, the spectral filter 24 of FIG. 6). In FIG. 7, the horizontal axis represents the wavelength of light and the vertical axis represents the transmittance of light (light transmittance). As described above, the spectral filter 24 of FIG. 6 includes the red light filters 24R, the blue light filters 24B, the green light filters 24G, and the near-infrared light filters 24IR. This configuration realizes the spectral characteristics shown in FIG. 7. According to the spectral characteristics, light incident on the light receiving device 20A is separated into red light (R light), blue light (B light), green light (G light), and IR light.

As shown in FIG. 7, each blue light filter 24B has a light transmittance peak at or near a wavelength of 470 nm. Thus, B light separated by the blue light filter 24B has an intensity peak at or near the wavelength of 470 nm. Each green light filter 24G has a light transmittance peak at or near a wavelength of 540 nm. Thus, G light separated by the green light filter 24G has an intensity peak at or near the wavelength of 540 nm. Each red light filter 24R has a light transmittance peak at or near a wavelength of 650 nm. Thus, R light separated by the red light filter 24R has an intensity peak at or near the wavelength of 650 nm. Each near-infrared light filter 24IR has a light transmittance peak at or near a wavelength of 850 nm. Thus, IR light separated by the near-infrared light filter 24IR has an intensity peak at or near the wavelength of 850 nm.

Reference is made back to FIG. 6. The solid-state image sensor 23A in the example of FIG. 6 further includes R pixels PIXR, B pixels PIXB, and G pixels PIXG in addition to the IR pixels PIXIR. As shown in FIG. 6, the blue light filters 24B cover the B pixels PIXB when viewed from the living body (the living body H). Thus, the B pixels PIXB receive the B light separated by the blue light filters 24B. The green light filters 24G cover the G pixels PIXG when viewed from the living body. Thus, the G pixels PIXG receive the G light separated by the green light filters 24G. The red light filters 24R cover the R pixels PIXR when viewed from the living body. Thus, the R pixels PIXR receive the R light separated by the red light filters 24R. The near-infrared light filters 24IR cover the IR pixels PIXIR when viewed from the living body. Thus, the IR pixels PIXIR receive the IR light separated by the near-infrared light filters 24IR.

As is apparent from the above description, first pixels may be realized, for example, by covering monochrome pixels with first filters. This description regarding first pixels applies similarly to pixels corresponding to other wavelength bands.

Figure 8:
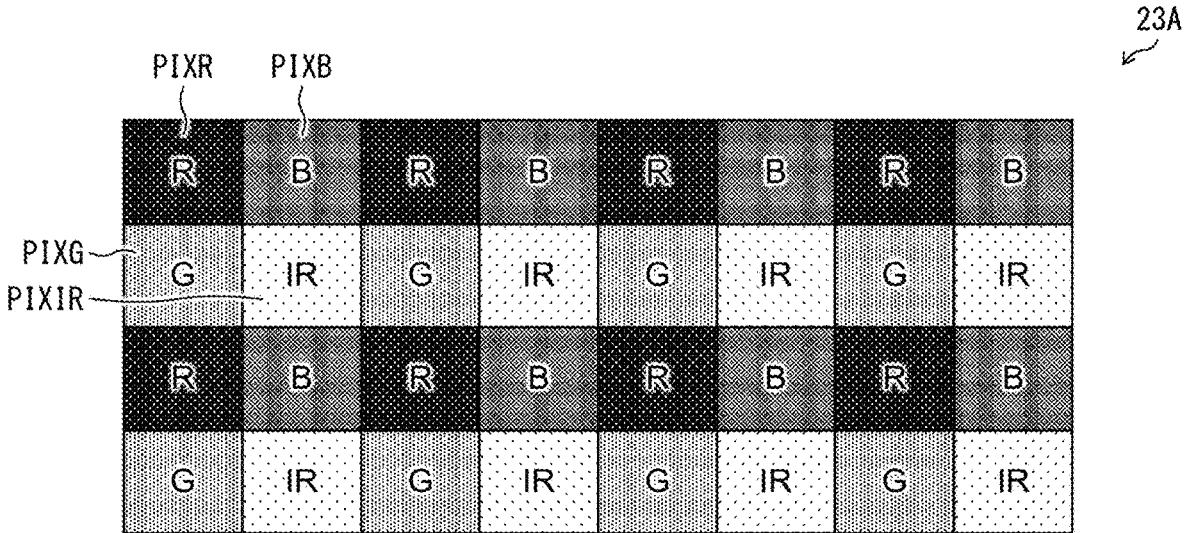
FIG. 8 is a schematic top view showing an example of an arrangement of pixels of each type in a solid-state image sensor of the second embodiment.

FIG. 8 is a schematic top view showing an example of an arrangement of pixels of each type in the solid-state image sensor 23A of FIG. 6. FIG. 8 can also be said as a schematic top view showing an example of an arrangement of each type of filters. Pixels of each type may be regularly arranged two-dimensionally as shown in FIG. 8. Thus, the arrangement of pixels of each type may be a two-dimensional array.

In the example of FIG. 8, the R pixels PIXR and the B pixels PIXB are arranged alternately in a row direction (a horizontal direction on the page). In each column to which the R pixels PIXR belong, the R pixels PIXR and the G pixels PIXG are alternately arranged in a column direction (a vertical direction on the page). On the other hand, in each column to which the B pixels PIXB belong, the B pixels PIXB and the IR pixels PIXIR are alternately arranged in a column direction. In this way, one specific pixel may be adjacent to one second pixel.

Effects of Biological Information Acquisition Device 2

The solid-state image sensor 23A has IR pixels and first pixels (e.g., R pixels) as specific pixels as described above. Thus, an image captured by the solid-state image sensor 23A includes (i) IR image components (near-infrared image components) corresponding to the IR pixels and (ii) first image components (e.g., R image components) corresponding to the first pixels.

The light absorption rate of hemoglobin in the IR wavelength band is higher than the light absorption rate in the first wavelength band as described above. Therefore, the biological information deriving unit 33 may correct the IR image components on the basis of the first image components. Next, the biological information deriving unit 33 may derive a pulse volume further on the basis of the corrected IR image components. Thus, a more accurate pulse volume can be acquired.

In an example, the biological information deriving unit 33 may subtract first image components in a frame of interest from IR image components in the frame of interest. According to this correction, noise components caused by body movements of the living body H can be effectively reduced in the IR image components because the IR image components and the first image components are synchronized. Noise components caused by fluctuations in the amount of environmental light can be effectively reduced in the IR image components.

In another example, the biological information deriving unit 33 may subtract first image components in a non-emission image frame (e.g., a reference frame) from the IR image components in the frame of interest. According to this correction, noise components caused by spectral fluctuations of environmental light can be effectively reduced in the IR image components.

The solid-state image sensor 23A further includes second pixels (e.g., B pixels and G pixels). Thus, an image captured by the solid-state image sensor 23A further includes second image components (e.g., B image components and G image components) corresponding to the second pixels.

As is apparent from the description of the first embodiment, the light absorption rate of hemoglobin in the second wavelength band is higher than the light absorption rate in the first wavelength band. Therefore, the biological information deriving unit 33 may further correct the IR image components on the basis of the second image components. Next, the biological information deriving unit 33 may derive a pulse volume further on the basis of the corrected IR image components.

Second image components in an emission image frame are expected to include more pulse volume components than first image components in the emission image frame. Therefore, the biological information deriving unit 33 may add second image components in a frame of interest to IR image components in the frame of interest as an example. Alternatively, the biological information deriving unit 33 may add the second image components multiplied by a predetermined weighting coefficient to the IR image components. According to this correction, pulse volume components can be increased, such that an even more accurate pulse volume can be acquired.

A typical example of hemoglobin contained in the human skin is oxyhemoglobin. It is known that the light absorption rate of oxyhemoglobin increases as the wavelength of light becomes shorter. Therefore, the weighting coefficient described above may be set, for example, on the basis of the light absorption characteristics of oxyhemoglobin.

Human skin contains melanin. However, it is difficult to identify the wavelength band of noise components derived from melanin in advance because there are large individual differences in the content of melanin in the skin. However, the biological information acquisition device 2 can effectively reduce noise components derived from melanin compared to the biological information acquisition device 1 by providing pixels of various types compared to the biological information acquisition device 1. As can be understood from this, the biological information acquisition device 2 can acquire even more accurate biological information.

The information processing device 30 may identify a skin region in an image, for example, using an arbitrary image recognition algorithm. The first wavelength band and the second wavelength band generally belong to the visible light wavelength band as described above. Thus, when the solid-state image sensor 23A has first pixels and second pixels, the information processing device 30 can easily identify a skin region on the basis of first image components and second image components.

Further, in the second embodiment, the biological information deriving unit 33 may derive IR light-based biological information (near-infrared light-based biological information) corresponding to IR image components on the basis of the IR image components. IR light has high penetration into human skin. Thus, IR light-based biological information is an example of biological information in a deep area of the skin. In this way, the biological information deriving unit 33 can also selectively acquire biological information in a deep area of the skin.

The biological information deriving unit 33 may also derive non-IR light-based biological information (non-near-infrared light-based biological information) corresponding to first image components and second image components on the basis of the first image components and the second image components. Non-IR light with shorter wavelengths than IR light has lower penetration into human skin than IR light. Thus, non-IR light-based biological information is an example of biological information in a shallow area of the skin. In this way, the biological information deriving unit 33 can also selectively acquire biological information in a shallow area of the skin.

The biological information deriving unit 33 may further derive final biological information (comprehensive biological information) on the basis of the IR light-based biological information and the non-IR light-based biological information. Namely, the biological information deriving unit 33 may combine IR light-based biological information and non-IR light-based biological information to derive final biological information (biological information integrating biological information in deep and shallow areas of the skin). Arbitrary numerical processing such as weighting and averaging may be performed in combining IR light-based biological information and non-IR light-based biological information.

The biological information deriving unit 33 may combine IR light-based biological information and non-IR light-based biological information to acquire even more accurate biological information as final biological information. The biological information deriving unit 33 may individually present the IR light-based biological information and the non-IR light-based biological information to the user (e.g., the living body H).

Third Embodiment

Figure 9:
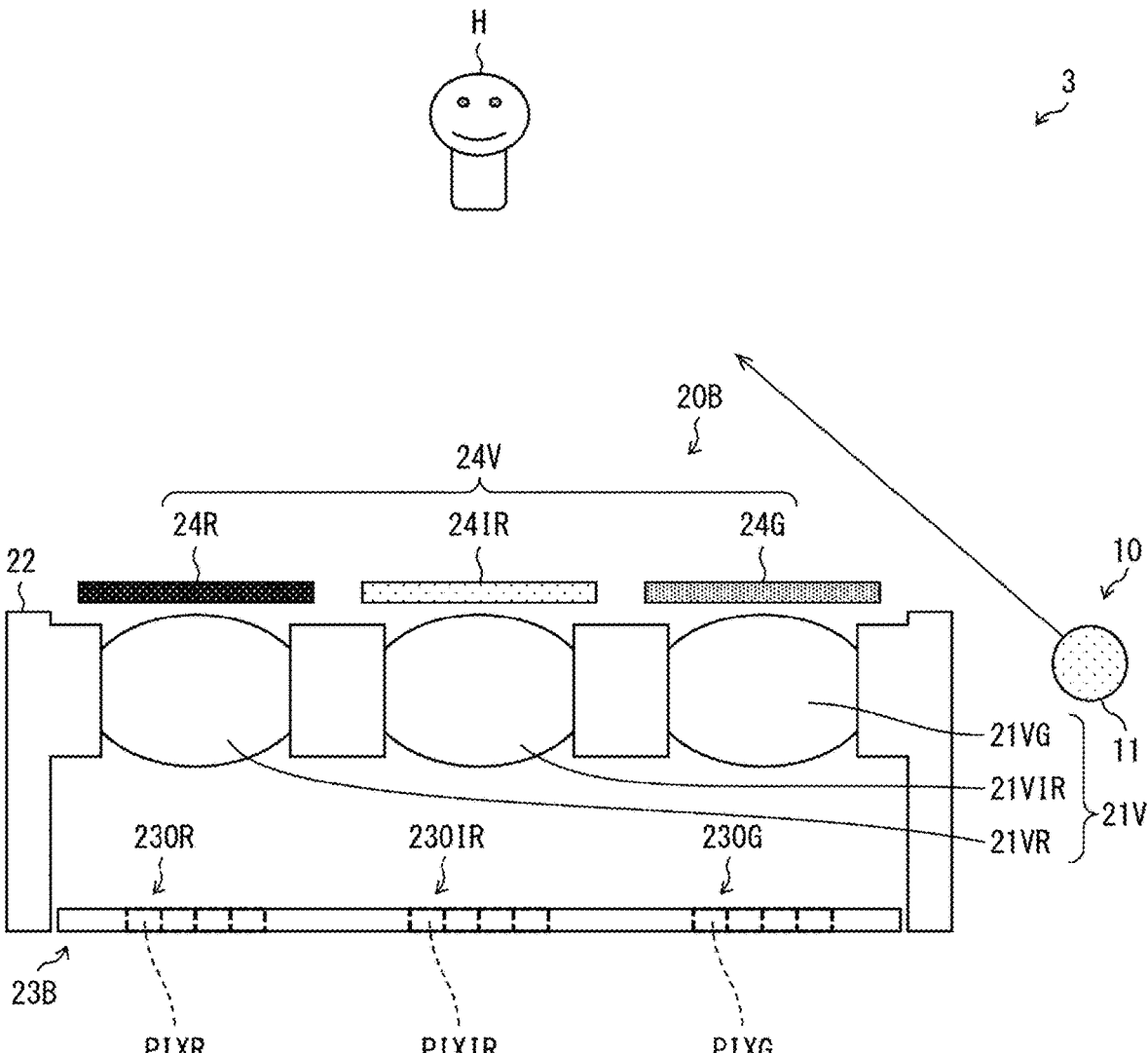
FIG. 9 is a schematic front view illustrating an example of a configuration of a light receiving device according to a third embodiment.

FIG. 9 is a schematic front view illustrating an example of a configuration of a light receiving device 20B in a biological information acquisition device 3 according to a third embodiment. FIG. 9 is a diagram corresponding to FIG. 6. A solid-state image sensor in the light receiving device 20B is referred to as a solid-state image sensor 23B. A spectral filter in the light receiving device 20B is referred to as a spectral filter 24V and a light guide member in the light receiving device 20B is referred to as a light guide member 21V.

The spectral filter 24V in the example of FIG. 9 is located closer to the living body than the light guide member 21V is. Thus, the positional relationship between the spectral filter and the light guide member is not limited to the example shown in FIG. 6. Unlike the example of FIG. 6, the spectral filter 24V may not include blue light filters 24B. Accordingly, the solid-state image sensor 23B may not have B pixels PIXB.

The light guide member 21V in the example of FIG. 9 includes a first light guide member 21VR, a second light guide member 21VG, and a third light guide member 21VIR. Thus, in the example of FIG. 9, an individual light guide member is provided for pixels of each type unlike the example of FIG. 6. According to the configuration of FIG. 9, the light guide members can be made smaller compared to the configuration of FIG. 6. Thus, for example, the light receiving device can be made thinner. The light receiving device can also be made lighter.

In the example of FIG. 9, the R pixels PIXR (first pixels), the G pixels PIXG (second pixels), and the IR pixels PIXIR may be provided corresponding to the first light guide member 21VR, the second light guide member 21VG, and the third light guide member 21VIR, respectively. Thus, for example, the solid-state image sensor 23B may have a first pixel region, a second pixel region, and an IR pixel region (a near-infrared pixel region) 230IR that are spaced apart from each other. An R pixel region 230R in FIG. 9 is an example of the first pixel region and a G pixel region 230G is an example of the second pixel region.

As shown in FIG. 9, the IR pixel region 230IR may have a plurality of the IR pixels PIXIR that are adjacent to each other. Similarly, the first pixel region may have a plurality of first pixels that are adjacent to each other. The second pixel region may also have a plurality of second pixels that are adjacent to each other. Thus, the R pixel region 230R may have a plurality of the R pixels PIXR that are adjacent to each other. The G pixel region 230G may also have a plurality of the G pixels PIXG that are adjacent to each other.

In the example of FIG. 9, a red light filter 24R is located closer to the living body than the first light guide member 21VR is. The red light filter 24R covers the R pixel region 230R when viewed from the living body. Thus, the first light guide member 21VR guides R light separated by the red light filter 24R to the R pixels PIXR. Similarly, the second light guide member 21VG guides G light separated by a green light filter 24G to the G pixels PIXG. The third light guide member 21VIR guides IR light separated by a near-infrared light filter 24IR to the IR pixels PIXIR.

Supplementary Information Regarding Third Embodiment

It is to be noted that the configuration of FIG. 9 is merely an example as is apparent to those skilled in the art. Thus, for example, the solid-state image sensor 23B may include B pixels PIXB instead of the G pixels PIXG. In this case, the spectral filter 24V may include a blue light filter 24B instead of the green light filter 24G.

In another example, the solid-state image sensor 23B may include both G pixels PIXG and B pixels PIXB. In this case, the spectral filter 24V may include both the blue light filter 24B and the green light filter 24G. When the solid-state image sensor 23B includes both G pixels PIXG and B pixels PIXB, the information processing device 30 can identify the skin region with higher accuracy than when the solid-state image sensor 23B includes only either G pixels PIXG or B pixels PIXB.

Example of Implementation Using Software

The functions of each of the biological information acquisition devices 1 to 3 (hereinafter referred to as a "device") are implemented by a program for causing a computer to function as the device, the program causing the computer to function as each control block of the device (particularly each unit included in the information processing device 30).

In this case, the device includes a computer including at least one control device (e.g., processor) and at least one storage device (e.g., memory) as hardware components for executing the program. Each function described in each of the above embodiments is implemented by the control device and the storage device executing the program.

The program may be recorded on one or more non-transitory computer-readable recording media. This recording medium may or may not be included in the above device. In the latter case, the program may be supplied to the device via any wired or wireless transmission medium.

Some or all of the functions of each of the control blocks described above can also be implemented by a logic circuit. For example, an integrated circuit in which a logic circuit functioning as each of the control blocks described above is formed is also included in the scope of the disclosure. The functions of each of the control blocks described above can also be implemented by, for example, using a quantum computer instead of or in addition to the integrated circuit.

Each process described in each of the above embodiments may be executed by artificial intelligence (AI). In this case, the AI may operate on the control device or may operate on another device (e.g., an edge computer or a cloud server).

Supplements

In a biological information acquisition device according to a first aspect is a biological information acquisition device that acquires biological information of a living body in a non-contact manner, the biological information acquisition device including a near-infrared light source configured to emit near-infrared light having an intensity peak in a near-infrared wavelength band of 760 nm or more and 1100 nm or less toward the living body, a solid-state image sensor configured to capture an image of the living body by receiving light arriving from the living body, and an information processing device configured to derive the biological information on the basis of the image, wherein the solid-state image sensor includes at least one specific pixel having a sensitivity peak in a specific wavelength band of 620 nm or more and 1100 nm or less, the information processing device is configured to repeatedly acquire (i) an emission image frame captured by the solid-state image sensor during an emission period of the near-infrared light source and (ii) a non-emission image frame captured by the solid-state image sensor during a non-emission period of the near-infrared light source, and the information processing device is configured to derive the biological information on the basis of the emission image frame and the non-emission image frame.

In a biological information acquisition device according to a second aspect of the disclosure, in the first aspect, an arbitrary one of a plurality of the emission image frames may be defined as a first emission frame of interest, an emission image frame following the first emission frame of interest may be defined as a second emission frame of interest, and the information processing device may be configured to obtain a signal value of a virtual emission image frame in the non-emission period between a time at which the first emission frame of interest is captured and a time at which the second emission frame of interest is captured through interpolation on the basis of a signal value of the first emission frame of interest and a signal value of the second emission frame of interest and derive the biological information further on the basis of the signal value of the virtual emission image frame.

In a biological information acquisition device according to a third aspect of the disclosure, in the first or second aspect, an arbitrary one of a plurality of the non-emission image frames may be defined as a first non-emission frame of interest, the non-emission image frame following the first non-emission frame of interest may be defined as a second non-emission frame of interest, and the information processing device may be configured to obtain a signal value of a virtual non-emission image frame in the emission period between a time at which the first non-emission frame of interest is captured and a time at which the second non-emission frame of interest is captured through interpolation on the basis of a signal value of the first non-emission frame of interest and a signal value of the second non-emission frame of interest and derive the biological information further on the basis of the signal value of the virtual non-emission image frame.

In a biological information acquisition device according to a fourth aspect of the disclosure, in any one of the first to third aspects, the specific pixel may include (i) a near-infrared pixel having a sensitivity peak in the near-infrared wavelength band and (ii) a first pixel having a sensitivity peak in a first wavelength band of 620 nm or more and 740 nm or less, the image may include (i) a near-infrared image component corresponding to the near-infrared pixel and (ii) a first image component corresponding to the first pixel, and the information processing device may be configured to correct the near-infrared image component on the basis of the first image component and derive the biological information further on the basis of the near-infrared image component after the correction.

In a biological information acquisition device according to a fifth aspect of the disclosure, in the fourth aspect, the solid-state image sensor may further include at least one second pixel having a sensitivity peak in a second wavelength band of 350 nm or more and 590 nm or less, the image may further include a second image component corresponding to the second pixel, and the information processing device may be configured to further correct the near-infrared image component on the basis of the second image component and derive the biological information further on the basis of the near-infrared image component after the correction.

In a biological information acquisition device according to a sixth aspect of the disclosure, in the fifth aspect, the information processing device may be configured to derive near-infrared light-based biological information corresponding to the near-infrared image component on the basis of the near-infrared image component.

In a biological information acquisition device according to a seventh aspect of the disclosure, in the fifth or sixth aspect, the information processing device may be configured to derive non-near-infrared light-based biological information corresponding to the first image component and the second image component on the basis of the first image component and the second image component.

In a biological information acquisition device according to an eighth aspect of the disclosure, in any one of the fifth to seventh aspects, one of the at least one specific pixel may be adjacent to one of the at least one second pixel.

In a biological information acquisition device according to a ninth aspect of the disclosure, in any one of the fifth to eighth aspects, the solid-state image sensor may have a near-infrared pixel region, a first pixel region, and a second pixel region that are spaced apart from each other, the near-infrared pixel region may include a plurality of the near-infrared pixels that are adjacent to each other, the first pixel region may include a plurality of the first pixels that are adjacent to each other, and the second pixel region may include a plurality of the second pixels that are adjacent to each other.

In a biological information acquisition device according to a tenth aspect of the disclosure, in any one of the first to ninth aspects, the information processing device may be configured to derive a pulse volume as the biological information.

While there have been described what are at present considered to be certain embodiments of the invention, it will be understood that various modifications may be made thereto, and it is intended that the appended claims cover all such modifications as fall within the true spirit and scope of the invention.

What is claimed is:

1. A biological information acquisition device that acquires biological information of a living body in a non-contact manner, the biological information acquisition device comprising:

a near-infrared light source configured to emit near-infrared light, having an intensity peak in a near-infrared wavelength band of 760 nm or more and 1100 nm or less, toward the living body;

a solid-state image sensor comprising at least one specific pixel having a sensitivity peak in a specific wavelength band of 620 nm or more and 1100 nm or less, the solid-state image sensor configured to capture one or more images of the living body by receiving light arriving from the living body; and an information processing device configured to:

repeatedly acquire (i) an emission image frame captured by the solid-state image sensor during an emission period of the near-infrared light source, and (ii) a non-emission image frame captured by the solid-state image sensor during a non-emission period of the near-infrared light source, derive the biological information based on the emission image frame and the non-emission image frame, wherein:

an arbitrary one of a plurality of emission image frames, including the emission image frame, is defined as a first emission frame of interest, and a next emission image frame following the first emission frame of interest is defined as a second emission frame of interest, obtain a signal value of a virtual emission image frame in the non-emission period between a time, at which the first emission frame of interest is captured, and a time, at which the second emission frame of interest is captured, through interpolation based on a signal value of the first emission frame of interest and a signal value of the second emission frame of interest, and further derive the biological information based on the signal value of the virtual emission image frame.

2. A biological information acquisition device that acquires biological information of a living body in a non-contact manner, the biological information acquisition device comprising:

a near-infrared light source configured to emit near-infrared light, having an intensity peak in a near-infrared wavelength band of 760 nm or more and 1100 nm or less, toward the living body;

a solid-state image sensor comprising at least one specific pixel having a sensitivity peak in a specific wavelength band of 620 nm or more and 1100 nm or less, the solid-state image sensor configured to capture one or more images of the living body by receiving light arriving from the living body; and an information processing device configured to:

repeatedly acquire (i) an emission image frame captured by the solid-state image sensor during an emission period of the near-infrared light source, and (ii) a non-emission image frame captured by the solid-state image sensor during a non-emission period of the near-infrared light source, derive the biological information based on the emission image frame and the non-emission image frame, wherein:

an arbitrary one of a plurality of non-emission image frames, including the non-emission image frame, is defined as a first non-emission frame of interest, and a next non-emission image frame following the first non-emission frame of interest is defined as a second non-emission frame of interest, obtain a signal value of a virtual non-emission image frame in the emission period between a time, at which the first non-emission frame of interest is captured, and a time, at which the second non-emission frame of interest is captured, through interpolation based on a signal value of the first non-emission frame of interest and a signal value of the second non-emission frame of interest, and further derive the biological information based on the signal value of the virtual non-emission image frame.

3. A biological information acquisition device that acquires biological information of a living body in a non-contact manner, the biological information acquisition device comprising:

a near-infrared light source configured to emit near-infrared light, having an intensity peak in a near-infrared wavelength band of 760 nm or more and 1100 nm or less, toward the living body;

a solid-state image sensor comprising at least one specific pixel having a sensitivity peak in a specific wavelength band of 620 nm or more and 1100 nm or less, the solid-state image sensor configured to capture one or more images of the living body by receiving light arriving from the living body; and an information processing device configured to:

repeatedly acquire (i) an emission image frame captured by the solid-state image sensor during an emission period of the near-infrared light source, and (ii) a non-emission image frame captured by the solid-state image sensor during a non-emission period of the near-infrared light source, derive the biological information based on the emission image frame and the non-emission image frame, wherein:

the at least one specific pixel comprises (i) a near-infrared pixel having a sensitivity peak in the near-infrared wavelength band, and (ii) a first pixel having a sensitivity peak in a first wavelength band of 620 nm or more and 740 nm or less, and an image of the one or more images comprises (i) a near-infrared image component corresponding to the near-infrared pixel and (ii) a first image component corresponding to the first pixel, correct the near-infrared image component based on the first image component, and further derive the biological information based on the near-infrared image component after the correction.

4. The biological information acquisition device according to claim 3, wherein:

the solid-state image sensor further comprises at least one second pixel having a sensitivity peak in a second wavelength band of 350 nm or more and 590 nm or less, the image further comprises a second image component corresponding to the second pixel, and the information processing device is further configured to:

further correct the near-infrared image component on the basis of the second image component, and derive the biological information further based on the near-infrared image component after the correction.

5. The biological information acquisition device according to claim 4, wherein the information processing device is further configured to derive near-infrared light-based biological information corresponding to the near-infrared image component based on the near-infrared image component.

6. The biological information acquisition device according to claim 4, wherein the information processing device is further configured to derive non-near-infrared light-based biological information corresponding to the first image component and the second image component based on the first image component and the second image component.

7. The biological information acquisition device according to claim 4, wherein one of the at least one specific pixel is adjacent to one of the at least one second pixel.

8. The biological information acquisition device according to claim 4, wherein:

the solid-state image sensor comprises a near-infrared pixel region, a first pixel region, and a second pixel region that are spaced apart from each other, the near-infrared pixel region comprises a plurality of near-infrared pixels, including the near-infrared pixel, that are adjacent to each other, the first pixel region comprises a plurality of first pixels, including the first pixel, that are adjacent to each other, and the second pixel region comprises a plurality of second pixels, including the at least one second pixel, that are adjacent to each other.

9. The biological information acquisition device according to claim 1, wherein the information processing device is further configured to derive a pulse volume as the biological information.

* * * * *